United States Patent
Mannstadt et al.

(10) Patent No.: US 7,680,379 B2
(45) Date of Patent: Mar. 16, 2010

(54) BROADBAND LIGHT SOURCE IN PARTICULAR FOR SHORT COHERENCE INTERFEROMETRY

(75) Inventors: Wolfgang Mannstadt, Münster-Sarmsheim (DE); Bernd Drapp, Reutlingen (DE)

(73) Assignee: Schott AG, Mainz (DE)

( * ) Notice: Subject to any disclaimer, the term of this patent is extended or adjusted under 35 U.S.C. 154(b) by 0 days.

(21) Appl. No.: 10/953,441

(22) Filed: Sep. 29, 2004

(65) Prior Publication Data

US 2005/0265405 A1 Dec. 1, 2005

(30) Foreign Application Priority Data

Jun. 1, 2004 (DE) .................. 10 2004 026 931

(51) Int. Cl.
*G02B 6/00* (2006.01)
*G02B 6/02* (2006.01)

(52) U.S. Cl. ..................... 385/122; 385/125
(58) Field of Classification Search .................. 385/122
See application file for complete search history.

(56) References Cited

U.S. PATENT DOCUMENTS

| | | | | |
|---|---|---|---|---|
| 5,976,885 | A * | 11/1999 | Cohenford et al. ............ | 436/63 |
| 6,097,870 | A | 8/2000 | Ranka et al. .................. | 385/127 |
| 6,236,779 | B1 * | 5/2001 | Kafka et al. .................. | 385/31 |
| 6,419,810 | B1 * | 7/2002 | Tanaka et al. ................ | 205/73 |
| 6,611,643 | B2 * | 8/2003 | Birk et al. ..................... | 385/33 |
| 6,788,862 | B2 * | 9/2004 | Aitken et al. ................. | 385/122 |
| 6,796,699 | B2 * | 9/2004 | Birk et al. .................... | 362/556 |
| 2002/0050564 | A1 * | 5/2002 | Birk et al. .................... | 250/306 |
| 2003/0174985 | A1 * | 9/2003 | Eggleton et al. ............. | 385/125 |
| 2003/0215199 | A1 * | 11/2003 | Aitken et al. ................. | 385/122 |
| 2005/0094954 | A1 * | 5/2005 | Pickrell et al. ............... | 385/123 |
| 2005/0117841 | A1 * | 6/2005 | Braun et al. .................. | 385/27 |
| 2005/0122580 | A1 * | 6/2005 | Birk et al. .................... | 359/389 |

FOREIGN PATENT DOCUMENTS

GB 2 386 434 9/2003

OTHER PUBLICATIONS

"*Visible Continuum Generation in Air-Silica Microstructure Optical Fibers with Anomalous Dispersion at 800 nm*", Ranka, et al., Optic Letters, Jan. 1, 2000 vol. 25, No. 1, pp. 25-27.
"*Ultrahigh-resolution optical coherence tomography by broadband continuum generation from a photonic crystal fiber*", Wang, et al., Optics Letters, vol. 28, No. 3, Feb. 1, 2003.
"*The relation between temperature gradients and structural perfection of single-crystal $Bi_{12}SiO_{20}$ and $BI_{12}TiO_{20}$ fibers grown by the LHPG method*", Prokofiev, et al., Jan. 1995, Optical Materials 4, pp. 433-436.
"*Optical devices based on liquid crystal photonic bandgap fibres*", Larson, et al., Oct. 6, 2003, vol. 11, No. 20, Ooptics Express, pp. 2589-2596.
"*White-light supercontinuum generation with 60-ps pump pulses in a photonic crystal fiber*", Coen, et al., 2001, Optics Letters, vol. 26, No. 17, Sep. 1, 2001, pp. 1356-1358.
"*All-silica single-mode optical fiber with photonic crystal cladding*", Knight, et al., Optics Letters, vol. 21, No. 19, Oct. 1, 1996, pp. 1547-1549.

* cited by examiner

*Primary Examiner*—Tina M Wong
*Assistant Examiner*—Rhonda S Peace
(74) *Attorney, Agent, or Firm*—Ohlandt, Greeley, Ruggiero & Perle, L.L.P.

(57) ABSTRACT

The invention relates to an arrangement for generating a broadband spectrum which can be used in particular as a light source for short coherence interferometry. The arrangement comprises a laser, in particular a laser diode, for generating a short light pulse of wavelength $\lambda_p$ and a microstructured optical fiber (1) with a high nonlinearity, which has a zero dispersion of the group velocity in the vicinity of the wavelength $\lambda_p$ and an anomalous dispersion, as well as means for introducing the light pulse into the microstructured optical fiber.

27 Claims, 3 Drawing Sheets

BROADBAND LIGHT SOURCE IN PARTICULAR FOR SHORT COHERENCE INTERFEROMETRY

BACKGROUND OF THE INVENTION

1. Field of the Invention

The invention relates to an arrangement for generating a broadband spectrum which can be used in particular as a light source for short coherence interferometry.

2. Description of Related Art

Light sources with a short coherence length and a broadband spectrum are required, for example, in three-dimensional surface shape recording and in optical coherence tomography (OCT). OCT represents a noninvasive imaging method which makes the topography of surfaces and structures in scattering media visible. Light in the near IR is used for the examination of, for example, biological tissue, on account of its greater penetration depth into the tissue.

The measurement principle is based on an optical interferometer which determines the scattering power and depth position of the structures with a high resolution. The resolution of the OCT is dependent, inter alia, on the light source used. In OCT, the photons scattered in the tissue are filtered out on the basis of their interference properties. This requires a light beam with the shortest possible coherence length (but >0) and a broadband spectrum in the near IR. The three-dimensional resolution in the beam direction corresponds to the coherence length of the light used. The greater the coherence length, the greater the volumetric region from which information is backscattered. In modern OCT systems, the resolution is up to 10 micrometers. Resolutions of approx. 10 micrometers can be achieved, for example, using commercially available OCT appliances with superluminescent diodes which emit in the near IR. Although these diodes have a lower light efficiency than comparable laser diodes, their coherence length is short and they therefore allow a good resolution to be achieved in the appliance.

However, for many applications, for example in tumor therapy, an improved resolution at cellular level is required but cannot be achieved using commercially available appliances.

Furthermore, it is known to generate what is known as a supercontinuum by introducing intensive, ultrashort light pulses into a nonlinear optical medium.

In this context, photonic crystal fibers (PCF) are of increasing interest. These fibers comprise microstructured fibers, for example formed from a fiber core and a microstructured fiber cladding with a periodic structure (photonic band gap fiber), as described by J. C. Knight et al. in Optics Letters, Vol. 21, No. 19, P. 15-47 (October 1996), or a nonperiodic structure, as disclosed by U.S. Pat. No. 5,802,236, which surrounds the core and runs along the fiber length. Suitable structuring and formation of the fiber cladding and dimensioning of the fiber core give rise to index conduction of the radiation in the fiber. The radiation can be concentrated with a high intensity in the core by employing an effective refractive index difference between the fiber core and the fiber cladding (5% to 20%). These fibers typically comprise microstructured silicon oxide fibers.

The third-order nonlinear effects ($\chi^{(3)}$) which are essential to the generation of a supercontinuum, such as the self-phase modulation, only occur with short light pulses with a high peak intensity. Investigations carried out by Ranka, Windeler, Stenz in *Optics Letters*, Vol. 25, No. 25 (2000) have shown that sufficiently high field intensities to activate nonlinear processes in order to generate a supercontinuum in microstructured silicon oxide fibers can be achieved using femtosecond laser pulses.

Since the intensity of the light pulse corresponds to the ratio of pulse power to cross-sectional area of the fiber, and since the pulse power is determined by the ratio of pulse energy to pulse duration, to achieve nonlinear effects it is possible, within the context of what is technically feasible, either to shorten the pulse duration and/or to increase the pulse energy, for example by increasing the repetition rate of a laser, and/or to reduce the cross-sectional area of the fiber core of the fiber.

An output spectrum which covers the visible region and the near IR can be achieved with a core diameter of approx. 2 micrometers in microstructured silicon oxide fibers with an anomalous dispersion, as described for example in U.S. Pat. No. 6,097,870, and with a 100 femtosecond laser pulse from a titanium-sapphire laser (typical pulse energy 1 to 12 nJ, pulse power approx. 8 kW). For propagation of the pulse through the fiber, the geometry of the fiber (core, cladding structure) has to be adapted to the wavelength of the laser pulse, in such a manner that the zero dispersion of the group velocity is approximately at the wavelength of the laser pulse.

Therefore, the resolution of measurement arrangements used for short coherence interferometry could be increased by using Ti-sapphire lasers, but such lasers are large, unwieldy, unstable and expensive and are therefore unsuitable for use in a light source for OCT appliances or for other commercial short coherence measuring appliances.

BRIEF SUMMARY OF THE INVENTION

Therefore, it is an object of the invention to provide a simple, stable, broadband light source with a short coherence. Another object of the invention is to provide a simple and stable light source for short coherence interferometry measuring appliances, in particular for OCT, which allows a high level of measurement accuracy.

The object is achieved by an arrangement as described in claim 1, while advantageous configurations are given in further claims.

The light source according to the invention, which generates a broadband spectrum, comprises a laser for generating a short light pulse of wavelength $\lambda_p$ and a microstructured optical fiber which has a zero dispersion of the group velocity in the vicinity of (i.e. with a possible deviation of approx. ±20% from $\lambda_p$) the wavelength $\lambda_p$ and an anomalous dispersion, as well as means for introducing the light pulse into the microstructured optical fiber.

With a microstructured optical fiber which preferably has pronounced nonlinear optical properties, i.e. which has a radiation-intensity-dependent refractive index n (I)=$n_0$+$n_2$*I at the wavelength of the introduced light pulse $\lambda_p$, where the nonlinearity factor of the fiber is preferably $n_2 \geq 2*10^{-20}$ cm$^2$/W, it is possible to generate a broadband spectrum even using a laser diode which has light pulses in the picosecond range.

This eliminates, for example, complex and expensive sapphire lasers as have hitherto been required to generate femtosecond pulses as the input pulse into microstructured fibers for generating a broadband spectrum.

The optical nonlinearity of the fiber is determined on the one hand by its structure but on the other hand also by the material of the fiber, and therefore the microstructured optical fiber preferably consists of a nonlinear optical material with a high material nonlinearity factor $\chi^{(3)}$. This factor, in conjunction with the fiber geometry, determines the abovementioned nonlinearity factor of the fiber $n_2$.

Suitable materials for the microstructured optical fiber with a high $\chi^{(3)}$ are preferably materials formed from a multicomponent glass, a multicomponent glass-ceramic, a single-crystal material, a polycrystalline material, a plastic-matrix composite and/or a liquid-crystal material. The fiber may also be composed of a plurality of these materials.

In further suitable embodiments, the optical material may have isotropic and/or anisotropic properties.

In a further advantageous embodiment, the microstructured optical fiber comprises-at least one nonoxidic multicomponent glass, in particular a chalcogenide glass which contains at least As and Sn.

Further suitable materials for the microstructured optical fiber are materials which comprise at least one oxidic multicomponent glass, in particular silicate glasses which include at least one element selected from the group consisting of alkali metals ($Li_2O$, $Na_2O$, $K_2O$, $Rb_2O$, $Cs_2O$) and/or at least one element selected from the group consisting of alkaline-earth metals (MgO, CaO, SrO, BaO).

It is preferable for the oxidic multicomponent glass also to comprise at least one further element selected from the following group: $Al_2O_3$, $B_2O_3$, PbO, ZnO, $TiO_2$, $ThO_2$, $ZrO_2$, $La_2O_3$, $CeO_2$ and $P_2O_5$.

Heavy flint glass which includes the components $SiO_2$ and PbO and at least one of the components $Al_2O_3$, $B_2O_3$, $TiO_2$, $ThO_2$, $La_2O_3$, BaO, $Li_2O$, $Na_2O$ or $K_2O$, in particular SF57 comprising 24.5% by weight of $SiO_2$, 74.5% by weight of PbO, 0.4% by weight of $Na_2O$ and 0.6% by weight of $K_2O$, is a particularly suitable material with a high $\chi^{(3)}$ for the microstructured fiber.

In further suitable embodiments, the microstructured optical fiber may comprise at least one oxidic multicomponent glass-ceramic which includes crystal phases of strontium niobate, potassium hydrogen phosphate (KTP), BBO, LBO, $LiIO_3$, $LiNbO_3$, $KnbO_3$, $AgGaS_3$, $AgGaSe_2$, PPLN and/or $BaTiO_3$ or a plastic-matrix composite comprising an oxidic multicomponent glass and plastics based on PMMA (polymethyl methacrylate), PC (polycarbonate), PA (polyamide) or PE (polyethylene).

Furthermore, in particular the fiber core may comprise at least one single-crystal material formed from strontium niobate, potassium hydrogen phosphate (KTP), BBO, LBO, $LiIO_3$, $LiNbO_3$, $KnbO_3$, $AgGaS_3$, $AgGaSe_2$, PPLN or $BaTiO_3$ or a polycrystalline material comprising strontium niobate, potassium hydrogen phosphate (KTP), BBO, LBO, $LiIO_3$, $LiNbO_3$, $KnbO_3$, $AgGaS_3$, $AgGaSe_2$, PPLN and/or $BaTiO_3$ or a liquid crystal which includes a polymeric fraction with a mesogenic group within the main polymer chain or in a side chain which is branched off from the latter.

In addition to the demands relating to the material of the microstructured fiber with a view to achieving nonlinear effects (such as for example self-phase modulation) in the fiber with the lowest possible intensity of light pulse introduced, certain demands are also imposed on the geometry of the fiber for generating the broadband spectrum. The wavelength $\lambda_p$ of the light pulse introduced into the fiber and the geometry of the fiber determine the propagation of the light pulse through the fiber. To this end, the geometry, in particular the cross section of the fiber, has a design which produces a zero dispersion of the group velocity in the vicinity of the wavelength $\lambda_p$ of the light pulse and an anomalous dispersion of the light pulse in the microstructured fiber.

The microstructured optical fiber to this end preferably has a fiber core running along the length of the fiber and a structured fiber cladding arranged around the fiber core, in which case the fiber core in particular comprises a solid body and the fiber cladding comprises hollow structures running parallel to the fiber core.

In particular with a view to production of the microstructured fiber, which will be dealt with in more detail in a subsequent section of the description, it is advantageous if the fiber core comprises a solid rod and the fiber cladding comprises tubes arranged uniformly around the solid rod, preferably so as to form a hexagonal structure.

The minimum possible cross section of the fiber core is required in order to make the nonlinear effects become effective. For this purpose, in preferred embodiments of the invention the fiber core has a diameter of from 1 µm to 4 µm, and the surrounding tubes of the fiber cladding have a diameter of from 2 µm to 8 µm.

The microstructured optical fiber, in particular comprising the abovementioned materials and/or having the abovementioned small dimensions, is preferably produced using an IR drawing process in accordance with the U.S. application Ser. No. 10/858,461 in the name of the same Applicant and filed Jun. 1, 2004, entitled "Hot formed articles and method and apparatus for hot-forming", and the content of disclosure of this application is incorporated by reference in its entirety. This method makes it possible to draw high-precision microstructured fibers from corresponding preforms made from "difficult" materials, with the semi-homogenous temperature distribution and heating over the cross section of the fiber (<0.5 K/mm) at a low temperature during the drawing operation allowing effective and accurate manufacture.

To generate the desired nonlinear effects as are required to generate the broadband spectrum, the light pulse introduced must have a suitably high intensity. Given a high fiber nonlinearity, in particular $n_2 \geq 2*10^{-20}$ $cm^2/W$, and a small cross section of the fiber core of the microstructured fiber, in particular with a diameter of from 1 µm to 4 µm, it is preferable for a laser diode to be used to generate the short light pulse to be introduced into the fiber, since the intensity of the light pulse of the laser diode is already sufficient under these conditions.

With laser diodes which have a pulse duration of from 1 picosecond to 10 nanoseconds, preferably from 10 picoseconds to 100 picoseconds, and emit light pulses with a wavelength $\lambda_p$ in the range from 500 nm $\leq \lambda_p \leq$ 1800 nm, preferably a wavelength $\lambda_p$=1065 nm, it is possible, by introducing these light pulses into the microstructured fiber, to generate broadband spectra with a wavelength range from 400 nm to 2000 nm, in particular from 700 nm to 1300 nm. Spectra within these wavelength ranges are particularly suitable for optical coherence tomography (OCT), since light with these wavelengths can readily penetrate into tissue which is to be examined.

In one suitable embodiment of the invention, the means for introducing the light pulse into the microstructured optical fiber comprise a free-beam optical system, comprising a positioning unit and an imaging optical system for beam focusing, preferably a microscope objective.

Further suitable means for introducing the light pulse into the microstructured optical fiber comprise a coupling optical waveguide and a plug connection for connecting the coupling optical waveguide to the microstructured fiber.

To introduce the light pulse with the minimum possible losses, the plug connection preferably has a guide which orients the coupling optical waveguide and the microstructured optical fiber parallel to one another.

A guide of this nature is preferably designed as a ferrule. The ferrule is a small, highly accurate guide tube within the plug connection, which holds the ends of the fibers to be connected such that they are precisely axially aligned with one another and at the same time protects them. This ring may be made from various materials, for example glass, ceramic, plastic or metal.

In a further advantageous embodiment, the means for introducing the light pulse into the microstructured optical fiber comprise a coupling optical waveguide and a splice connection, by means of which the coupling optical waveguide and microstructured fiber are permanently joined.

The light source according to the invention is used as a light source for short coherence interferometry, in particular as a light source for OCT.

BRIEF DESCRIPTION OF THE SEVERAL VIEWS OF THE DRAWINGS

The invention is explained in more detail on the basis of the following drawings, in which.

DETAILED DESCRIPTION OF THE INVENTION

Figure 2:
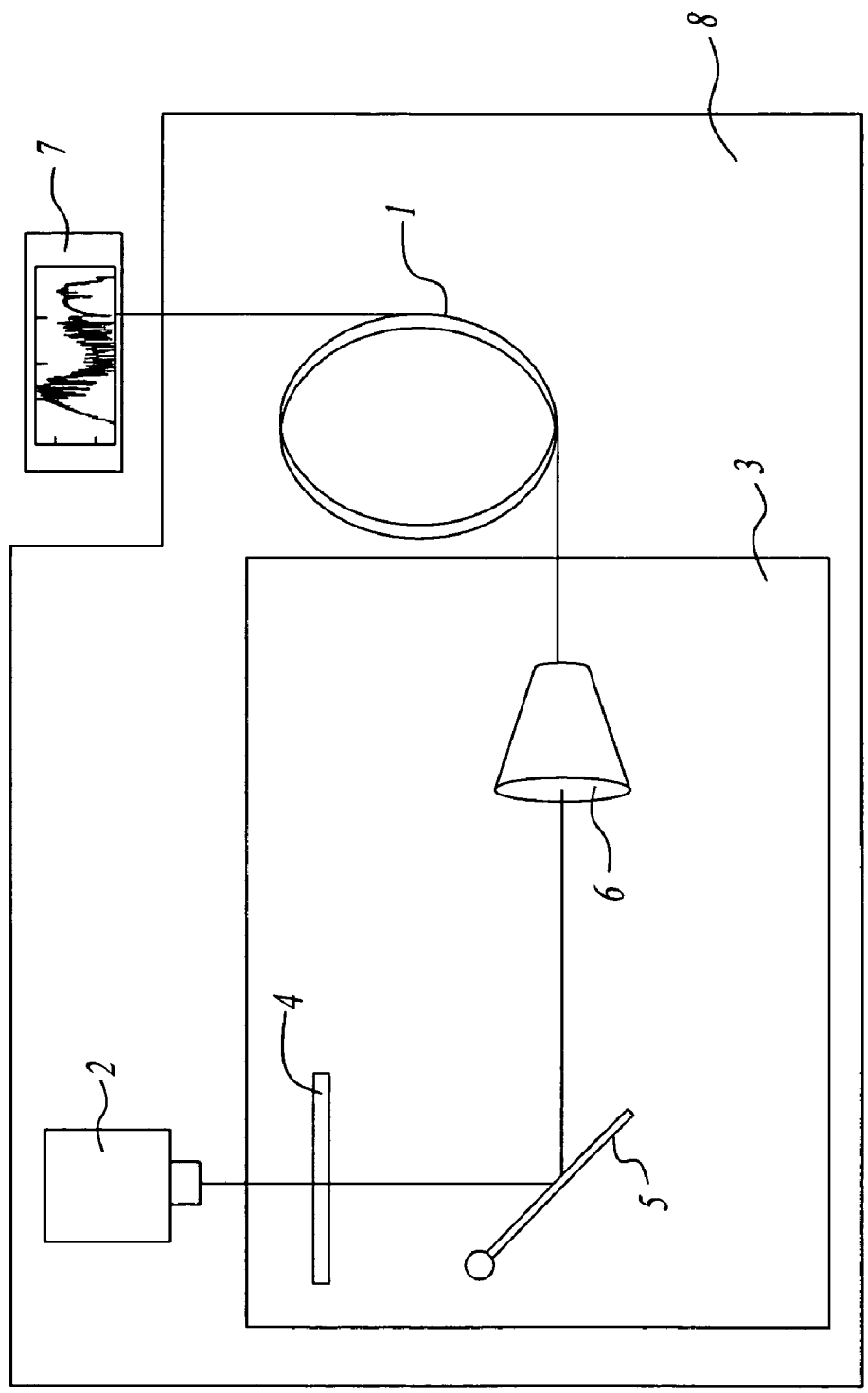
FIG. 2 shows a light source according to the invention.

FIG. 2 illustrates the diagrammatic structure of a light source (8) according to the invention illustrated by way of example. This light source comprises a laser diode (2), means (3) for introducing a light pulse and a microstructured optical fiber (1).

The laser diode (2) emits light pulses of wavelength $\lambda_p$=1065 nm in the direction of the means (3) for introducing the light pulse.

According to FIG. 2, the means (3) for introducing the light pulse comprise a diaphragm (4), a mirror (5) for directing the light pulse onto the microscope objective (6), which focuses the light pulse and introduces it into the microstructured optical fiber (1).

Figure 1:
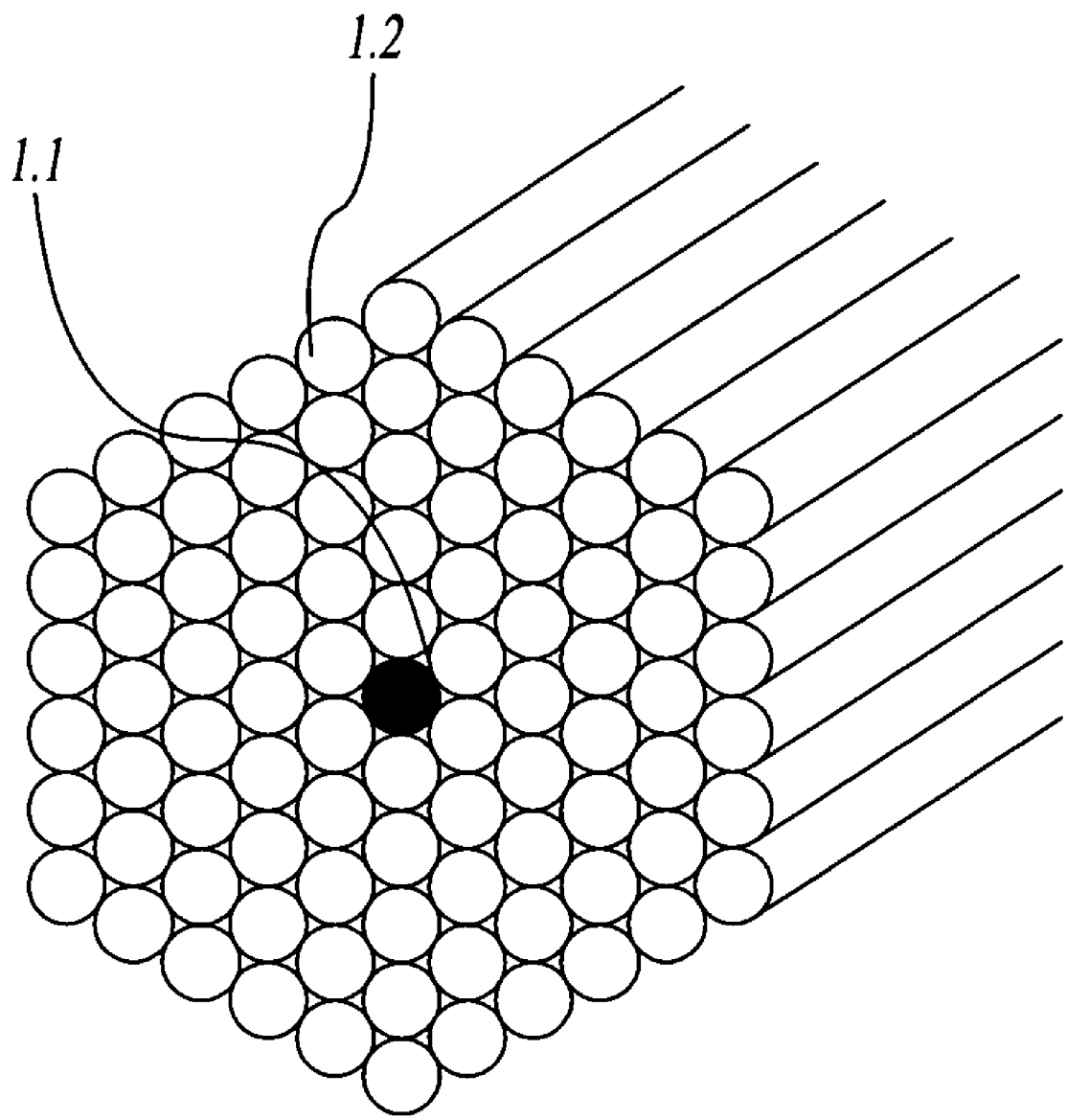
FIG. 1 diagrammatically depicts a microstructured optical fiber.

The microstructured optical fiber (1), which is diagrammatically depicted in section in FIG. 1, comprises a fiber core (1.1), which is designed as a solid rod, and tubes (1.2), which are arranged uniformly around the fiber core (1.1) and form the fiber cladding. The tubes (1.2) are arranged in a plurality of layers around the fiber core (1.1), in such a manner that they form a hexagonal structure. Structural arrangements of this type allow the pulse to propagate through the microstructured optical fiber (1).

The fiber material is SF57 comprising 24.5% by weight of $SiO_2$, 74.5% by weight of PbO, 0.4% by weight of $Na_2O$ and 0.6% by weight of $K_2O$.

The orders of magnitude of the microstructures are to be matched to the wavelength $\lambda_p$=1065 nm of the light pulses of the laser diode (2) and the material nonlinearity factor of the fiber material $\chi^{(3)}$, in such a manner that the microstructured optical fiber (1) has a zero dispersion of the group velocity in the vicinity of the wavelength $\lambda_p$ and an anomalous dispersion.

The configuration of the fiber geometry is known per se to the person skilled in the art and has been described, for example, by Barkou, Broeng and Bjarklev in "Dispersion properties of photonic bandgap guiding fibers", Optical Fiber Communication Conference, paper FG5, 1999 and by R. D. Meade, A. M. Rappe, K. D. Brommer, J. D. Joannopoulos and O. L. Alerhand in "Accurate theoretical analysis of photonic band-gap materials", Phys. Rev. V 48, 8434-8437 (1993).

The diameter of the fiber core (1.1) is 2.8 µm, the diameter of the tubes (1.2) is 2.9 µm, with the total diameter of the microstructured optical fiber (1) being 125 µm.

The accurate production of this microstructured optical fiber (1) from a heavy flint glass as described above is carried out using an IR drawing process in accordance with U.S. application Ser. No. 10/858,461 filed on Jun. 1, 2004.

Once the introduced light pulse has passed through the microstructured optical fiber (1), it has an output spectrum of from 700 nm to 1300 nm with a substantially uniform intensity. The output spectrum was recorded using a spectrometer (7).

This arrangement provides a stable and broadband light source (8) with a simple structure and a short coherence which can be used, for example, in OCT appliances. This arrangement is selected by way of example; consequently, further embodiments are possible within the scope of the present invention.

Figure 3:
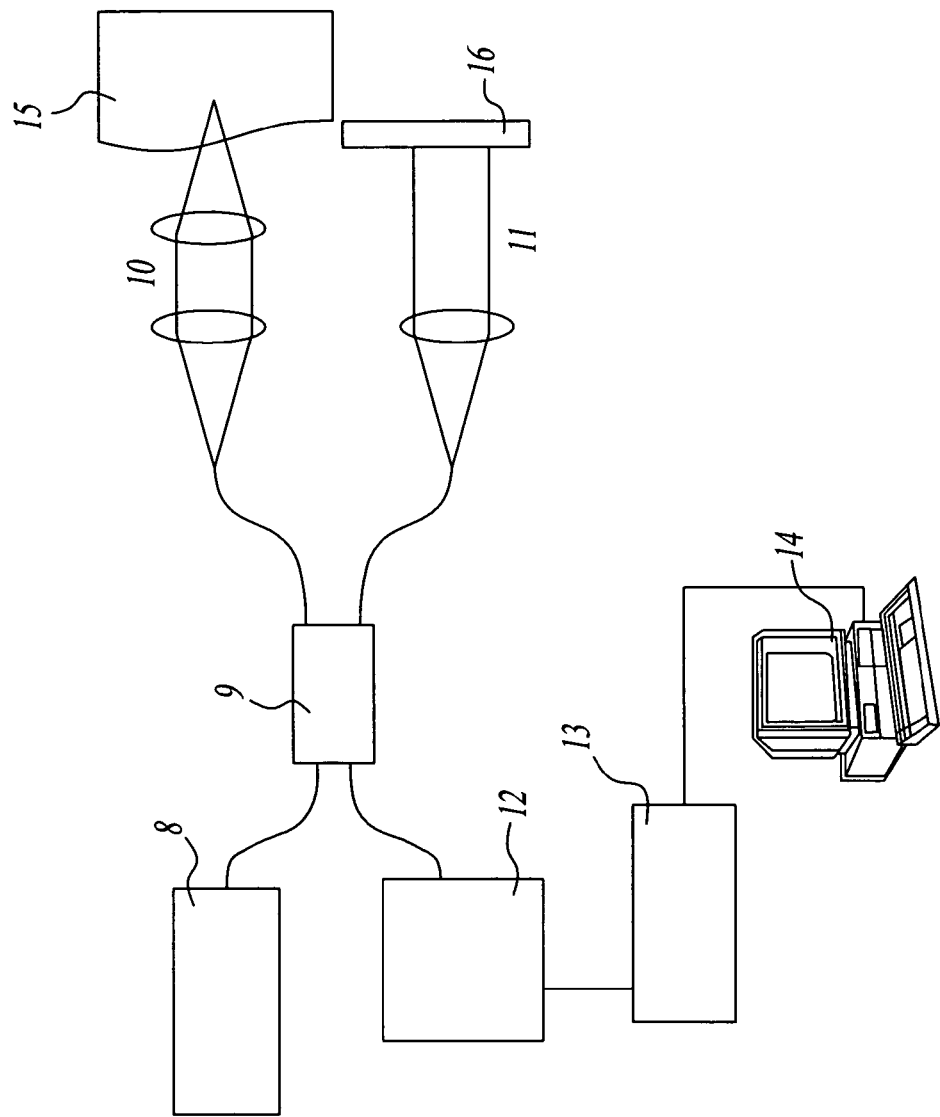
FIG. 3 shows the diagrammatic structure of an OCT arrangement.

FIG. 3 shows the use of the light source (8) according to the invention in an OCT arrangement. The OCT arrangement comprises the light source (8) which emits light with a spectrum in the range from 700 nm to 1300 nm. This light is diverted, via optical waveguides and a 2×2 coupler (9) via a collimator (10), onto the biological specimen (15) to be examined and is then diverted via a lens (11) onto a reference mirror (16). The light which is scattered and reflected from the specimen (15) and the light reflected from the reference mirror (16) are fed in superimposed form, via the 2×2 coupler (9), to the detector unit (12). The detector unit (12) determines the spectrum of the superimposition and uses an electronic processing unit (13) to display it as an image on a monitor (14).

Application areas for OCT are in particular in medicine, for example in early diagnosis of cancer or skin examinations. In these cases, reflections at the interfaces between materials with different refractive indices (membrane, cell layers, organ boundaries) are measured and in this way a three-dimensional image is reconstructed. On account of the high bandwidth of the light source (8) according to the invention, resolutions in the submicrometer range are possible, so that it is possible to produce subcellular structures.

The invention claimed is:

1. An optical coherence tomography appliance comprising:
    a light source which has a broadband spectrum, said light source comprising:
    a laser diode for generating a short light pulse of wavelength $\lambda_p$;
    a microstructured optical fiber having a zero dispersion of the group velocity in the vicinity of the wavelength $\lambda_p$ and an anomalous dispersion;
    means for directing the short light pulse from the laser diode into the microstructured optical fiber; and
    means for measuring an optical coherence tomography of a material or structure, based on the short light pulse received by the microstructured optical fiber, wherein the microstructured optical fiber comprises a nonlinear optical material having at least one material selected from the group consisting of a multicomponent glass-ceramic, an oxidic multicomponent glass-ceramic, a nonlinear optical material made from a single-crystal material, a polycrystalline material, a liquid-crystal material, and a heavy flint glass, and
    wherein the heavy flint glass comprises $SiO_2$ and PbO and at least one further component selected from the group consisting of: $Al_2O_3$, $B_2O_3$, $TiO_2$, $ThO_2$, $La_2O_3$, BaO, $Li_2O$, $Na_2O$, and $K_2O$.

2. The optical coherence tomography appliance as claimed in claim 1, wherein the microstructured optical fiber has a radiation-intensity-depentent refractive index n where n(l)= $n_0 + n_2 * 1$ at the wavelength $\lambda_p$, where $n_2 \geq 2*10^{-20}$ cm²/W.

3. The optical coherence tomography appliance as claimed in claim 1, wherein the nonlinear optical material has isotropic and/or anisotropic properties.

4. The optical coherence tomography appliance as claimed in claim 1, wherein the microstructured optical fiber comprises heavy flint glass consisting of heavy flint glass SF57 comprising:
24.5% by weight of $SiO_2$,
74.5% by weight of PbO,
0.4% by weight of $Na_2O$, and
0.6% by weight of $K_2O$.

5. The optical coherence tomography appliance as claimed in claim 1, wherein the microstructured optical fiber comprises multicomponent glass-ceramic including at least one component having a crystal phase, said at least one component being selected from the group consisting of strontium niobate, potassium hydrogen phosphate (KTP), BBO, LBO, $LilO_3$, $LiNbO_3$, $KnbO_3$, $AgGaS_3$, $AgGaSe_2$, PPLN, and $BaTiO_3$.

6. The optical coherence tomography appliance as claimed in claim 1, wherein the microstructured optical fiber comprises at least one single-crystal including an element selected from the group consisting of strontium niobate, potassium hydrogen phosphate (KTP), BBO, LBO, $LilO_3$, $LiNbO_3$, $KnbO_3$, $AgGaS_3$, $AgGaSe_2$, PPLN, and $BaTiO_3$.

7. The optical coherence tomography appliance as claimed in claim 1, wherein the microstructured optical fiber comprises at least one polycrystalline material which includes a plurality of elements selected from the group consisting of strontium niobate, potassium hydrogen phosphate (KTP), BBO, LBO, $LilO_3$, $LiNbO_3$, $KnbO_3$, $AgGaS_3$, $AgGaSe_2$, PPLN, and $BaTiO_3$.

8. The optical coherence tomography appliance as claimed in claim 1, wherein the microstructured optical fiber comprises at least one nonlinear optical material formed from a plastic-matrix composite.

9. The optical coherence tomography appliance as claimed in claim 8, wherein the plastic-matrix composite comprises an oxidic multicomponent glass and at least one plastic which is based on an element selected from the group consisting of PMMA (polymethyl methacrylate), PC (polycarbonate), PA (polyamide), and PE (polyethylene).

10. The optical coherence tomography appliance as claimed in claim 1, wherein the microstructured optical fiber comprises a liquid crystal which includes at least one polymeric fraction with a mesogenic group within the main polymer chain or in a side chain branching off from it.

11. The optical coherence tomography appliance as claimed in claim 1, wherein the microstructured optical fiber has a fiber core running along the length of the fiber and a structured fiber cladding arranged around the fiber core.

12. The optical coherence tomography appliance as claimed in claim 11, wherein the fiber core comprises a solid body and the fiber cladding comprises hollow structures running parallel to the fiber core.

13. The optical coherence tomography appliance as claimed in claim 11, wherein the fiber core comprises a solid rod and the fiber cladding comprises tubes arranged uniformly around the solid rod.

14. The optical coherence tomography appliance as claimed in claim 13, wherein the fiber core has a diameter of from 1 µm to 4 µm, and the tubes have a diameter of from 2 µm to 8 µm.

15. The optical coherence tomography appliance as claimed in claim 1, wherein the broadband spectrum comprises a wavelength range from 400 nm to 2000 nm.

16. The optical coherence tomography appliance as claimed in claim 1, wherein the broadband spectrum comprises a wavelength range from 700 nm to 1300 nm.

17. The optical coherence tomography appliance as claimed in claim 1, wherein the means for directing the short light pulse comprises a free-beam optical system, said free-beam optical system comprising a positioning unit and an imaging optical system for beam focusing.

18. The optical coherence tomography appliance as claimed in claim 1, wherein the means for directing the short light pulse comprises a coupling optical waveguide and a plug connection.

19. The optical coherence tomography appliance as claimed in claim 18, wherein the plug connection has a guide for orienting the coupling optical waveguide and the microstructured optical fiber parallel to one another.

20. The optical coherence tomography appliance as claimed in claim 19, wherein the plug connection includes a metal ferrule.

21. The optical coherence tomography appliance as claimed in claim 1, wherein the means for directing the short light pulse comprises a coupling optical waveguide and a splice connection.

22. The optical coherence tomography appliance as claimed in claim 1, wherein the light source is useable for short coherence interferometry.

23. A short-coherence measuring appliance comprising:
a light source having a broadband spectrum, wherein the light source includes a laser diode for generating a short light pulse of wavelength $\lambda_p$;
a microstructured optical fiber having a zero dispersion of the group velocity in the vicinity of the wavelength $\lambda_p$, and an anomalous dispersion;
a directing device for directing the short light pulse from the laser diode into the microstructured optical fiber; and
means for measuring an optical coherence tomography of a material or structure, based on the short light pulse received by the microstructured optical fiber,
wherein the microstructured optical fiber comprises a nonlinear optical material having at least one material selected from the group consisting of a multicomponent glass-ceramic, an oxidic multicomponent glass-ceramic, a nonlinear optical material made from a single-crystal material, a polycrystalline material, a liquid-crystal material, and a heavy flint glass, and
wherein the heavy flint glass comprises $SiO_2$ and PbO and at least one further component selected from the group consisting of: $Al_2O_3$, $B_2O_3$, $TiO_2$, $ThO_2$, $La_2O_3$, BaO, $Li_2O$, $Na_2O$, and $K_2O$.

24. An optical coherence tomography appliance comprising:
a light source which has a broadband spectrum, comprising:
a laser diode for generating a short light pulse of wavelength $\lambda_p$;
a microstructured optical fiber having a zero dispersion of the group velocity in the vicinity of the wavelength $\lambda_p$, and an anomalous dispersion;
means for directing the short light pulse from the laser diode into the microstructured optical fiber; and
means for measuring an optical coherence tomography of a material or structure, based on the short light pulse received by the microstructured optical fiber.

25. The light source as claimed in claim 24, wherein the short light pulse of the laser diode has a pulse duration of from 1 picosecond to 10 nanoseconds.

26. The light source as claimed in claim 24, wherein the wavelength $\lambda_p$ is in the range from 500 nm $\leq \lambda_p \leq$ 1800 nm.

27. The light source as claimed in claim 24, wherein the wavelength $\lambda_p$ is 1065 nm.

* * * * *